US00PP17888P2

(12) United States Plant Patent
Olesen

(10) Patent No.: US PP17,888 P2
(45) Date of Patent: Jul. 31, 2007

(54) ROSE PLANT 'POULPAH030'

(50) Latin Name: ***Rosa* hybrid**
Varietal Denomination: Poulpah030

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 11/337,254

(22) Filed: Jan. 19, 2006

(51) Int. Cl.
*A01H 5/00* (2006.01)

(52) U.S. Cl. ..... Plt./101

(58) Field of Classification Search ..... Plt./101
See application file for complete search history.

*Primary Examiner*—Kent Bell
*Assistant Examiner*—Annette H. Para

(57) ABSTRACT

A new miniature rose plant which has abundant, white flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa* hybrid.
Variety denomination: 'Poulpah030'.

SUMMARY OF THE INVENTION

The present invention constitutes a new and distinct variety of miniature rose plant which originated from a controlled crossing between a female seed parent, an unnamed seedling, and a male parent named 'KORklevia', described and illustrated in U.S. Plant Pat. No. 11,232 issued on Feb. 22, 2000. The two parents were crossed and the resulting seeds were planted in a controlled environment. The new variety is named 'Poulpah030'.

The new rose may be distinguished from its seed parent, primarily by flower color. 'Poulpah030' is a yellow-white rose, while the seed parent is a yellow-orange rose.

The new variety may be distinguished from the pollen parent, by the following combination of characteristics:

1. 'KORklevia' has 25 to 30 flower petals, while 'Poulpah030' has 60 petals, 15 to 20 of which are petaloids.
2. Upper surfaces of the inner petals on 'KORklevia' are Yellow Group 16C while the same surfaces on 'Poulpah030' are Green-White Group 157A.

The objective of the hybridization of this rose variety for commercial culture was to create a new and distinct variety with unique qualities, such as:

1. Uniform and abundant white flowers with green guard petals;
2. Vigorous and compact growth;
3. Year-round flowering under glasshouse conditions;
4. Suitability for production from softwood cuttings in pots;
5. Durable flowers and foliage which makes a variety suitable for distribution in the floral industry.

This combination of qualities is not present in previously available commercial cultivars of this type and distinguish 'Poulpah030' from all other varieties of which we are aware.

As part of the rose development program, Mogens Nyegaard Olesen germinated the seeds from the aforementioned hybridization and conducted evaluations on the resulting seedlings in a controlled environment in Fredensborg, Denmark.

'Poulpah030' was selected by the inventor as a single plant from the progeny of the hybridization work done in June 2001.

Asexual reproduction of 'Poulpah030' by cuttings and traditional budding was first done by Mogens Nyegaard Olesen in the nursery in Fredensborg, Denmark in July 2002. This initial and other subsequent propagations conducted in controlled environments have demonstrated that the characteristics of 'Poulpah030' are true to type and are transmitted from one generation to the next.

BRIEF DESCRIPTION OF THE DRAWING

The accompanying color illustrations show as true as is reasonably possible to obtain in color photographs of this type, the typical characteristics of the buds, flowers, leaves, and stems of 'Poulpah030'. Specifically illustrated in the drawing:

FIG. 1.1; Flower buds at various stages of development;

FIG. 1.2; Sepals, receptacle, and pedicel;

FIG. 1.3; Flower petals detached, and open flower;

FIG. 1.4; Juvenile leaves;

FIG. 1.5; Mature leaves; and

FIG. 1.6; Bare stem.

DETAILED DESCRIPTION OF THE VARIETY

The following is a description of 'Poulpah030', as observed in its growth in glasshouse in Odense, Denmark in August 2005. Observed plants are 10 weeks of age. Color references are made using The Royal Horticultural Society (London, England) Colour Chart, 2001, except where common terms of color are used.

For a comparison, physical characteristics of the rose variety 'Poulhi012', a rose variety from the same inventors described and illustrated in U.S. Plant Pat. No. 14,742 issued on Apr. 27, 2004, are compared to 'Poulpah030' in Chart 1.

CHART 1

| | 'Poulpah030' | 'Poulhi012' |
|---|---|---|
| Petal Count | 60 petals, 15 to 20 of which are petaloids | 75 to 80 petals |
| Color of lower surface of guard petals | White Group 155A to Green-White Group 157A. Intonations of Yellow-Green Group 145A streaking the petal and petal margin. | Green-White Group 157C. |

FLOWER AND FLOWER BUD

Blooming habit: Continuous.

Flower bud:

*Size.*—Upon opening, 20 to 22 mm in length from base of receptacle to end of bud. Bud diameter is normally 12 mm.

*Bud form.*—Pointed ovoid.

*Bud color.*—As sepals unfold, petals are Yellow-Green Group 145C to 145B.

*Sepals.*—

*Inner surface.*—Color: Yellow-Green Group 147 A to Green Group 139A. At the apex, intonations of Greyed-Purple Group 183A observed. Surface: Weak pubescence.

*Outer surface.*—Color: Yellow-Green Group 147B and 146A. At the apex of the sepal, anthocyanic pigments the color of Greyed-Purple Group 183A observed. Texture: Somewhat rough with numerous stipitate glands.

*Sepal shape.*—Base is flat at the union with the receptacle. Strong foliaceous appendages on three of the five sepals. Sepal apex becomes broadened on some sepals. Size: 35 to 55 mm long×11 to 18 mm wide.

*Receptacle.*—Surface texture: Smooth, glabrous. Shape: Funnel to urn-shaped. Size: 6 mm (h)×8 mm (w). color: Yellow-Green Group 144A.

*Peduncle.*—Surface: Somewhat rough with stipitate glands. Length: 40 to 50 mm. Color: Yellow-Green Group 144A. Strength: Strong and rigid.

*Borne.*—Normally, flowers are borne singly.

Flower bloom:

*Fragrance.*—Light floral fragrance.

*Duration.*—As a pot plant, flowers may last up to 28 days.

*Size.*—Average flower diameter is 65 mm when open. Flower depth is normally 30 mm.

*Form.*—General shape is calathiform, with tightly packed petals. Shape of flower side view: Upon opening, upper part: Flat. Upon opening, lower part: Flat. Open flower, upper part: Flat. Open flower, lower part: Concave.

*Petalage.*—60 petals on average, 15 to 20 of which are petaloids.

Color:

*Upon opening, petals.*—Outermost petals: Upper Surface: White Group 155A to Green-White Group 157A. Intonations of Yellow-Green Group 145 A, found mainly on the outermost guard petals, streak along the petal and are found at the petal margins. Lower Surface: White Group 155A to Green-White Group 157A. Intonations of Yellow-Green Group 145A, found mainly on the outermost guard petals, streak along the petal and are found at the petal margins. Innermost petals: Upper Surface: Green-White Group 158C. Lower Surface: Yellow-White Group 158B to Yellow 4D. At the base of the petal, intonations of Orange-White Group 159A are blended in.

*Upon opening, basal petal spots.*—Upper Surface: Very light intonation of Yellow Group 4B at the point of petal attachment. Lower Surface: None observed.

*After opening, petals.*—Outermost petals: Upper Surface: Yellow-Green Group 145C to 145D at the basal and middle zone. Yellow-Green Group 145A at the petal apex. Lower Surface: Yellow-Green Group 145C to 145D at the basal and middle zone. Yellow-Green Group 145A at the petal apex. Intermediate petals: Upper Surface: Green-White Group 157A. Lower Surface: Green-White Group 157A. Occasionally, a faint streak the color of Red-Purple Group 73B is bisecting the petal. Innermost petals: Upper and Lower; Petal surfaces are Yellow-White Group 158C with light intonations of Yellow Group 4D. Occasionally, a faint streak the color of Red-Purple Group 73B is bisecting the petal.

*After opening, basal petal spots.*—Upper Surface: Yellow Group 4B. Lower Surface: Yellow Group 4B.

General tonality: On open flower Yellow-White Group 158C with light intonations the color of Yellow Group 4A towards the flower center. Outer whorl of petals has intonations of Yellow-Green Group 145A to 145C. The tonality does not change as the flower matures.

Petals:

*Petal reflex.*—Petals are somewhat reflexed.

*Petal edge.*—Entire. Very strong undulations of margin observed on the outer petals. The inner petals do not have undulations.

*Shape.*—Generally, round to broad orbicular. The apex varies from orbicular, cuspidate, to emarginate. The base is rounded.

*Size.*—25 to 30 mm in length by 25 to 45 mm wide.

*Texture.*—Outer petals are somewhat rough. Inner petals are smooth.

*Thickness.*—Average.

*Petaloids.*—Quantity: 15 to 20. Size: 18 to 22 mm (l)×8 to 22 mm (w). Shape: Broad elliptical and irregular. Normally petaloids have 1, occasionally 2 clefts at the margin. Color: Upper and lower petaloid surfaces are Yellow-White Group 158C with light intonations of Yellow-Group 4D. Occasionally, a faint streak the color of Red-Purple Group 73B is bisecting the petal. Basal petal spots are Yellow 4D.

Reproductive organs:

*Pollen.*—None observed.

*Anthers.*—Size: 2.5 mm long. Color: Yellow-White Group 158A. Quantity: 70 on average.

*Filaments.*—Color: Yellow Group 2A. Length: 6 mm.

*Pistils.*—Length: 5 to 7 mm long. Quantity: 75 on average.

*Stigmas.*—Superior in location, relative to the length of the filaments and the position of the anthers. Color: Greyed-Yellow Group 162D.

*Styles.*—Color: Greyed-Yellow Group 162D with intonations of Red-Purple Group 61B.

*Seed formation.*—Seeds not formed due to the method of culture.

PLANT

Plant growth: Moderate, upright, and somewhat bushy. When grown as a 12-15 cm pot plant on its own roots, the average height of the plant itself is 25 cm and the average width is 20 cm.

Stems:

*Color.*—Young wood: Yellow-Green Group 144A. Older wood: Yellow-Green Group 146A. Internodal Distance: 25 mm.

*Surface.*—Young wood: Smooth. Older wood: Smooth.

*Prickles.*—Incidence: 2 per 10 cm of stem. Size: 3 mm (l)×0.5 mm (w). Color: Greyed-Purple Group 183B. Shape: Upper and lower sides are flat.

Plant foliage: Normal number of leaflets on normal leaves in the middle of the stem: 5 leaflets.

*Compound leaf size.*—On average, 85 mm (l)×70 mm (w).

*Quantity.*—3 to 4 leaves per 10 cm of stem.

*Color.*—Mature foliage: Upper Leaf Surface: Yellow-Green Group 147A. Lower Leaf Surface: Yellow-Green Group 147B. Anthocyanic intonations the color of Greyed-Purple Group 187A observed on many leaf margins. Juvenile foliage: Upper Leaf Surface: Yellow-Green Group 146A with anthocyanin in the margins Greyed-Purple Group 183A. Lower Leaf Surface: Yellow-Green Group 147B with a faint overlay of Greyed-Purple 183A.

Plant leaves and leaflets:

*Stipules.*—Size: 10 mm in length. Shape: Linear, slightly broad based with outward extending apecies. Margins: Finely serrated with few stipitate glands. Color: Yellow-Green Group 146A.

*Petiole.*—Length: 18 mm on average. Diameter: 1.25 mm. Upper surface: Color: Greyed-Purple 187B. Observations: Few stipitate glands. Underneath: Color: Yellow-Green 146B. Observations: Few stipitate glands. Somewhat rough in texture.

*Rachis.*—Length: 25 mm on average. Upper surface: Color: Greyed-Purple Group 187B. Observations: Few stipitate glands. Underneath: Color: Yellow-Green Group 146B. Observations: Few stipitate glands. Somewhat rough in texture with small prickles.

*Leaflet.*—Margin: Serrated. Size: Terminal leaflets are normally 45 mm long by 28 mm wide. Shape: Generally ovate. The base shape is rounded. Apex is acuminate. Texture: Smooth, somewhat rugose. Thickness: Average to thin. Arrangement: Odd pinnate. Venation: Reticulate. Leaf Gloss: Matte finish.

Disease resistance: Average resistance to powdery and downy mildew, black spot, and *Botrytis* under normal growing conditions in Odense, Denmark.

It is claimed:

1. A new and distinct variety of rose plant of the miniature class named 'Poulpah030', substantially as illustrated and described herein, due to its abundant, white flowers, vigorous growth, compact habit, suitability for production from softwood cuttings in pots, and durable flowers and foliage which make the variety suitable for distribution in the floral industry.

* * * * *

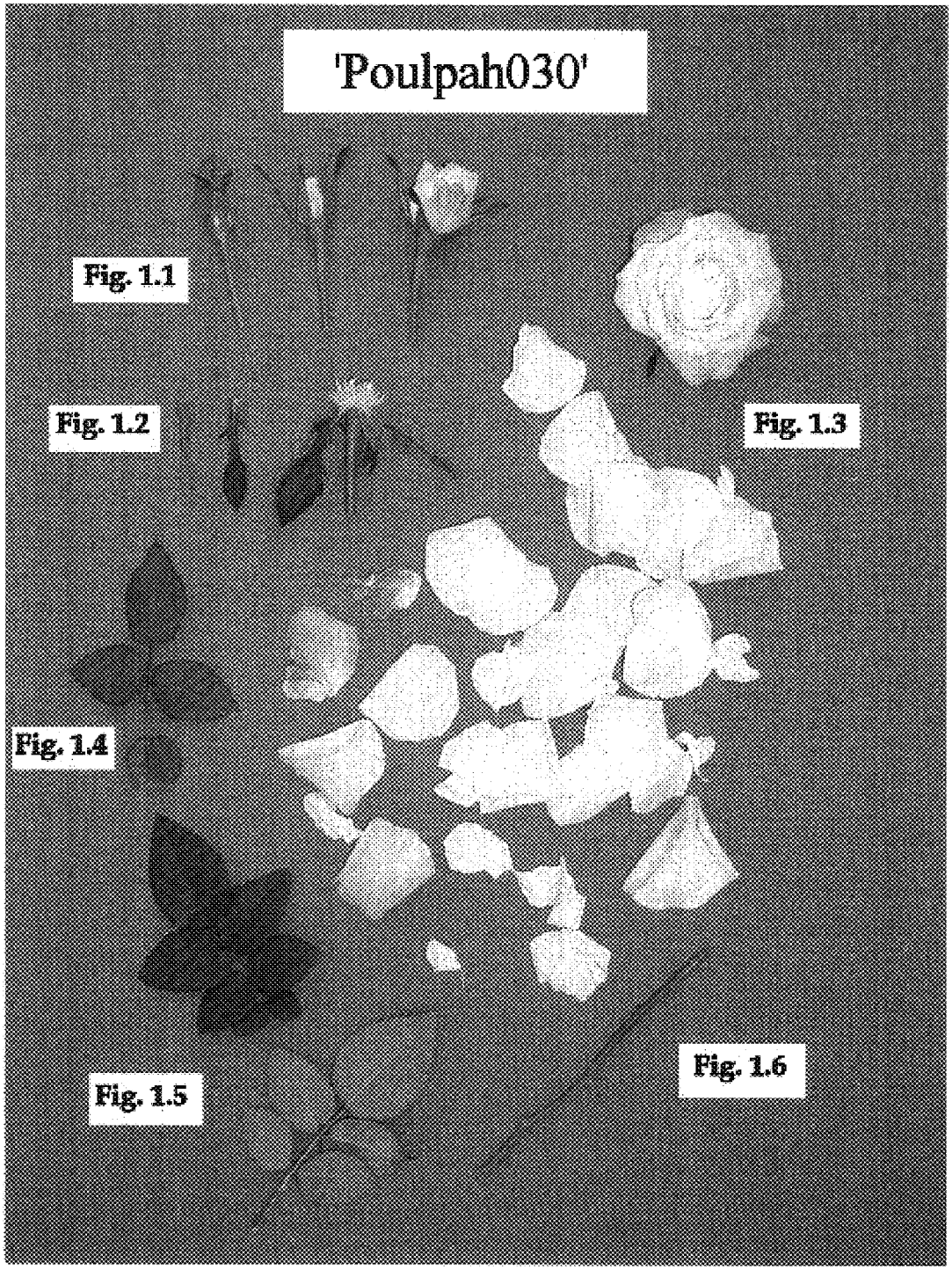
'Poulpah030'
Fig. 1.1
Fig. 1.2
Fig. 1.3
Fig. 1.4
Fig. 1.5
Fig. 1.6